United States Patent
Horie et al.

(10) Patent No.: US 6,937,333 B2
(45) Date of Patent: Aug. 30, 2005

(54) APPARATUS FOR MEASURING FILM THICKNESS FORMED ON OBJECT, APPARATUS AND METHOD OF MEASURING SPECTRAL REFLECTANCE OF OBJECT, AND APPARATUS AND METHOD OF INSPECTING FOREIGN MATERIAL ON OBJECT

(75) Inventors: Masahiro Horie, Kyoto (JP); Hideki Hayashi, Kyoto (JP); Fujikazu Kitamura, Kyoto (JP); Kumiko Akashika, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 133 days.

(21) Appl. No.: 10/652,071

(22) Filed: Sep. 2, 2003

(65) Prior Publication Data
US 2004/0075836 A1 Apr. 22, 2004

(30) Foreign Application Priority Data
Oct. 18, 2002 (JP) ..................................... P2002-303775

(51) Int. Cl.$^7$ ................................................ G01J 4/00
(52) U.S. Cl. ...................................... 356/369; 356/630
(58) Field of Search ................................ 356/369, 364, 356/630; 250/225

(56) References Cited

U.S. PATENT DOCUMENTS 5,748,305 A  5/1998  Shimono et al.
6,128,084 A * 10/2000  Nanbu et al. ............... 356/369
6,608,689 B1 * 8/2003  Wei et al. .................... 356/630

FOREIGN PATENT DOCUMENTS

| CN | 1104643 C | 4/2003 |
|----|-----------|--------|
| JP | S61-182507 | 8/1986 |
| JP | 9-15163 | 1/1997 |
| JP | H11-271027 | 10/1999 |

* cited by examiner

Primary Examiner—Gregory J. Toatley, Jr.
Assistant Examiner—Roy M. Punnoose
(74) Attorney, Agent, or Firm—McDermott Will & Emery LLP

(57) ABSTRACT

A film thickness measurement apparatus (1) comprises an ellipsometer (3) for acquiring a polarization state of a film on a substrate (9) and a light interference unit (4) for acquiring spectral intensity of the film on the substrate (9). In an optical system (45) of the light interference unit (4), a light shielding pattern (453a) is disposed in an aperture stop part (453), and an illumination light from a light source (41) is emitted to the substrate (9) through the optical system (45). A reflected light from the substrate (9) is guided to a light shielding pattern imaging part (43), where an image of the light shielding pattern (453a) is acquired. When the ellipsometer (3) performs a film thickness measurement, a tilt angle of the substrate (9) is obtained on the basis of the image of the light shielding pattern (453a) and a light receiving unit (32) acquires a polarization state of the reflected light. An calculation part (51) obtains a thickness of a film with high precision from the polarization state of the reflected light by using the obtained tilt angle.

3 Claims, 4 Drawing Sheets

APPARATUS FOR MEASURING FILM THICKNESS FORMED ON OBJECT, APPARATUS AND METHOD OF MEASURING SPECTRAL REFLECTANCE OF OBJECT, AND APPARATUS AND METHOD OF INSPECTING FOREIGN MATERIAL ON OBJECT

BACKGROUND OF THE INVENTION

1. Field of the Invention

The present invention relates to a technique to measure a thickness of a film formed on an object, technique to measure spectral reflectance of an object and a technique to inspect foreign material on an object.

2. Description of the Background Art

Conventionally adopted, as a method of measuring a thickness of a thin film formed on a surface of an object, is ellipsometry, or reflectance spectroscopy or a method which is called a white-light interferometric method without involving ellipsometry (hereinafter, these two methods are referred to as "white-light interferometric method and the like"). In general, the ellipsometry allows a film thickness measurement with high precision on a thin film and the white-light interferometric method and the like allow a measurement on a thicker film, as compared with the measurement by ellipsometry, or on a multilayer film.

Japanese Patent Application Laid Open Gazette No. 61-182507 discloses a method of specifying a thickness of a film on an object from a refractive index which is measured by an ellipsometer and an interfering wave which is obtained by an interferometer, where the ellipsometer and the interferometer are provided in one apparatus.

Japanese Patent Application Laid Open Gazette No. 11-271027 proposes a method for measuring a film thickness, where a range of thickness of a film on an object is specified by the white-light interferometric method and the like and the film thickness is measured by ellipsometry on the basis of the specified film thickness range.

In ellipsometry, however, since a wavelength and an incident angle of light emitted to an object is used in computation for obtaining a film thickness, it is necessary, for high-precision film thickness measurement, to precisely specify the wavelength of an incident light, keep a measurement surface of the object horizontal and so on. Further, since a measurement region is very small, when a microscopic foreign material (e.g., submicron particles) is attached to the surface of the object, it is impossible to perform a film thickness measurement with high precision.

On the other hand, in the white-light interferometric method the like, it is necessary to correct a measured value by using a reference object whose reflectance is known, and if the reflectance is changed due to natural oxidation of a surface of the reference object, it is impossible to appropriately correct the measured value.

SUMMARY OF THE INVENTION

It is a main object of the present invention to measure a thickness of a film formed an object with high precision.

The present invention is intended for a film thickness measurement apparatus for measuring a thickness of a film formed on an object.

According to the present invention, the film thickness measurement apparatus comprises a first light source for emitting a polarized light to an object, a light receiving part for receiving a reflected light of the polarized light from the object to acquire a polarization state of the reflected light, an calculation part for obtaining a thickness of a film on the object on the basis of the polarization state, a second light source for emitting an illumination light, an optical system for guiding the illumination light to the object and guiding a reflected light of the illumination light from the object to a predetermined position, a light shielding pattern disposed at a position almost optically conjugate to an aperture stop position on an optical path from the second light source to the object, and an imaging part for acquiring an image of the light shielding pattern formed on the predetermined position, and in the film thickness measurement apparatus, the calculation part obtains a tilt angle of the object on the basis of an output from the imaging part and obtains a thickness of the film from the polarization state, by using the tilt angle.

In the film thickness measurement apparatus of the present invention, it is possible to obtain a thickness of a film on an object while obtaining a tilt angle of the object.

According to a preferred embodiment, the film thickness measurement apparatus further comprises a filter disposed at a position almost optically conjugate to a field stop position on an optical path from the second light source to the object, and in the film thickness measurement apparatus, the filter cuts off a light of at least specific wavelength at a portion out of a portion corresponding to a microscopic region on the object. This makes it possible to obtain a tilt angle of the microscopic region on the object.

The present invention is also intended for a reflectance measurement apparatus for measuring spectral reflectance of a measurement object. The reflectance measurement apparatus is preferably used for measuring a film thickness of the measurement object.

According to the present invention, the reflectance measurement apparatus comprises a film thickness measurement part for measuring a thickness of a film on a reference object by ellipsometry, and a reflectance measurement part for irradiating the reference object and a measurement object with an illumination light to acquire respective spectral intensities of reflected lights from the reference object and the measurement object and then obtaining spectral reflectance of the measurement object, and in the reflectance measurement apparatus, the reflectance measurement part comprises an calculation part for calculating spectral reflectance of the reference object on the basis of the thickness of the film on the reference object, which is measured by the film thickness measurement part, and obtaining the spectral reflectance of the measurement object with reference to the spectral reflectance of the reference object.

The reflectance measurement apparatus of the present invention makes it possible to appropriately obtain spectral reflectance of a measurement object.

The present invention is further intended for another film thickness measurement apparatus. According to the present invention, the film thickness measurement apparatus comprises a light source for emitting a polarized light to an object, a light receiving part for receiving a reflected light of the polarized light from the object to acquire a polarization state of the reflected light, an calculation part for obtaining a thickness of a film on the object on the basis of the polarization state, a switching mechanism for guiding a light from the light source to a predetermined position during non-measurement periods, and a wavelength measurement part for acquiring a wavelength of the light guided to the predetermined position, and in the film thickness measurement apparatus, the calculation part obtains the thickness of the film on the object by using the wavelength acquired by the wavelength measurement part.

The film thickness measurement apparatus of the present invention makes it possible to obtain a thickness of a film on an object with high precision while obtaining a wavelength of light from a light source.

The present invention is still further intended for a foreign material inspection apparatus for inspecting the presence or absence of foreign material on a substrate.

According to the present invention, the foreign material inspection apparatus comprises a light source for emitting a light to a substrate at a predetermined incident angle, a light receiving part for acquiring intensity of a p-polarized component of a reflected light from the substrate, and a judgment part for judging the presence or absence of foreign material on the substrate on the basis of the intensity of the p-polarized component.

The foreign material inspection apparatus of the present invention makes it possible to quickly and easily inspect the presence or absence of foreign material on a substrate. The foreign material inspection apparatus is preferably used for measuring spectral reflectance of a substrate and a thickness of a film on the substrate, and this improves the precision of measurement result.

The present invention is also directed to methods applied for the apparatuses above mentioned.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
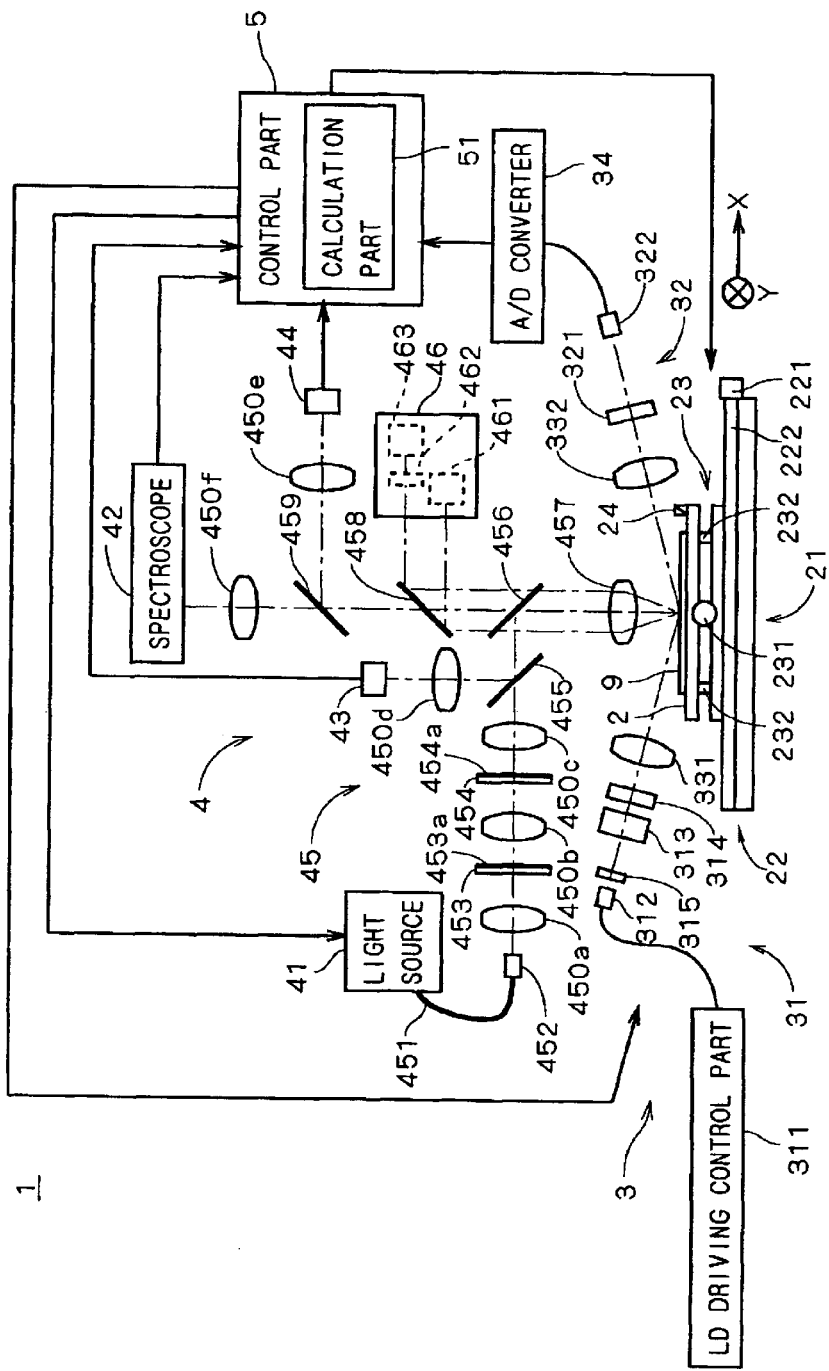
FIG. 1 is a view showing a schematic construction of a film thickness measurement apparatus.

FIG. 1 is a view showing a schematic construction of a film thickness measurement apparatus 1 in accordance with a first preferred embodiment of the present invention. The film thickness measurement apparatus 1 comprises a stage 2 on which a semiconductor substrate (hereinafter, referred to as "substrate") 9 on which a multilayer film (this film may be a single-layer one) is formed is disposed, an ellipsometer 3 for acquiring information used to perform ellipsometry on the film on the substrate 9, a light interference unit 4 for acquiring spectral intensity of a light (reflected light) from the substrate 9, a control part 5 constituted of a CPU for various computations, memories for storing various information and the like, and a stage moving mechanism 21 for moving the stage 2 relatively to a position irradiated with light by the ellipsometer 3 and the light interference unit 4.

The ellipsometer 3 has a light source unit 31 for emitting a polarized light to the substrate 9 and a light receiving unit 32 for receiving the reflected light from the substrate 9 to acquire a polarization state of the reflected light. Data indicating the acquired polarization state is outputted to the control part 5.

The light source unit 31 has a semiconductor laser (LD) 312 for emitting a light beam and an LD driving control part 311 for controlling an output of the semiconductor laser 312, and the light beam from the semiconductor laser 312 enters a polarizing filter 313. The polarizing filter 313 exracts a linearly polarized light out of the light beam and a quarter-wave plate (hereinafter, referred to as "λ/4 plate") 314 generates a circularly polarized light. The light from the λ/4 plate 314 is guided to a surface of the substrate 9 on the stage 2 through a lens 331 as a predetermined incident angle (e.g., 72 to 80 degrees). Thus, the light source unit 31 is constituted of the LD driving control part 311, the semiconductor laser 312, the polarizing filter 313 and the λ/4 plate 314 and emits the circularly polarized light to the substrate 9. An electro-magnetic shutter 315 for shutting out the light beam is provided in the light source unit 31 (specifically, on an optical path between the semiconductor laser 312 and the polarizing filter 313) to perform an ON/OFF control of emission of light to the substrate 9.

The reflected light from the substrate 9 is guided to a rotating analyzer 321 through a lens 332, the transmitted light is guided to a photodiode 322 while the rotating analyzer 321 rotates about an axis parallel to an optical axis, and a signal indicating the intensity of the received light is outputted to the control part 5 through an A/D converter 34. Thus, the light receiving unit 32 is constituted of the rotating analyzer 321 and the photodiode 322, and the polarization state of the reflected light is acquired by associating the output of the photodiode 322 with a rotation angle of the rotating analyzer 321.

The light interference unit 4 has a light source 41 for emitting a white light as an illumination light, a spectroscope 42 for dispersing the reflected light from the substrate 9, a light shielding pattern imaging part 43 for acquiring an image of a light shielding pattern discussed later, a substrate imaging part 44 for performing an imaging of an irradiation position of illumination light on the substrate 9 and an optical system 45. The optical system 45 guides the illumination light from the light source 41 to the substrate 9 and also guides the reflected light from the substrate 9 to the spectroscope 42, the light shielding pattern imaging part 43 and the substrate imaging part 44.

Specifically, the illumination light from the light source 41 is introduced to one end of an optical fiber 451 and led out from a lens 452 provided at the other end thereof. The outgoing illumination light is guided to an aperture stop part 453 through a lens 450a. A predetermined light shielding pattern 453a (e.g., a cross-shaped calibration mark) is provided at the aperture stop part 453. The illumination light is guided to a field stop part 454 through a lens 450b with part thereof corresponding to the light shielding pattern 453a being cut off.

The illumination light whose field is limited by the field stop part 454 is guided to a half mirror 455 through a lens 450c, going through the half mirror 455, and is further guided to a half mirror 456. The illumination light reflected by the half mirror 456 is emitted to the surface of the substrate 9 through an objective lens 457. At this time, the extent of an irradiation region of the illumination light on the substrate 9 corresponds to the limitation of field by the field stop part 454, but an image of the light shielding pattern of the aperture stop part 453 is not formed on the substrate 9.

The reflected light from the substrate 9 is guided to the half mirror 456 through the objective lens 457, and part of the light is reflected towards the half mirror 455. The reflected light is further reflected by the half mirror 455 and received by the light shielding pattern imaging part 43 through a lens 450d. In an optical system from the light shielding pattern 453a, through the surface of the substrate 9, to the light shielding pattern imaging part 43, the position of the light shielding pattern imaging part 43 is optically conjugate to the light shielding pattern 453a, an image of the light shielding pattern 453a is formed on the light shielding pattern imaging part 43 and image data of the light shielding pattern 453a is outputted to the control part 5.

The reflected light through the half mirror 456, further going through a half mirror 458, is guided to a half mirror 459 and part of the light is reflected. The reflected light goes through a lens 450e and is guided to the substrate imaging part 44 and received thereby. Since the position of the substrate imaging part 44 is optically conjugate to the positions of the field stop part 454 and the surface of the substrate 9, the substrate imaging part 44 performs an imaging of the irradiation position of the illumination light on the substrate 9 and the acquired image data is outputted to the control part 5.

The light through the half mirror 459 is guided to the spectroscope 42 through a lens 450f and the spectral intensity of the reflected light is obtained. Data of the spectral intensity is outputted to the control part 5. Thus, the optical system 45 is constituted of the lenses 450a to 450f and 452, the optical fiber 451, the aperture stop part 453, the field stop part 454, the half mirrors 455, 456, 458 and 459, and the objective lens 457.

The light interference unit 4 further has an autofocus detection unit (hereinafter, referred to as "AF detection unit") 46 for detecting a distance between the objective lens 457 and the surface of the substrate 9. The AF detection unit 46 has a semiconductor laser 461 for emitting a light beam and an AF detection part 463 for detecting a position of received light by a PSD element, and the light beam emitted from the semiconductor laser 461 enters the surface of the substrate 9 through the optical system 45. A reflected light of the light beam from the substrate 9 is guided to a cylindrical lens 462 of the AF detection unit 46 through the optical system 45 and further guided to the AF detection part 463.

The AF detection part 463 detects the distance between the objective lens 457 and the surface of the substrate 9 from the position of the light received thereby, and the distance between the objective lens 457 and the surface of the substrate 9 is controlled constant by an elevator mechanism (not shown) provided in the stage 2. At this time, the distance between the objective lens 457 and the surface of the substrate 9 is a distance where parallel rays of light entering the objective lens 457 form an image on the surface of the substrate 9 (i.e., focal length).

The stage moving mechanism 21 has an X-direction moving mechanism 22 for moving the stage 2 in an X direction of FIG. 1 and a Y-direction moving mechanism 23 for moving the stage 2 in a Y direction. The X-direction moving mechanism 22 comprises a motor 211 and a ball screw (not shown), and with rotation of the motor 221, the Y-direction moving mechanism 23 moves in the X direction of FIG. 1 along guide rails 222. The Y-direction moving mechanism 23 has the same constitution as the X-direction moving mechanism 22, and with rotation of a motor 231, the stage 2 is moved by a ball screw (not shown) in the Y direction along guide rails 232.

A mirror 24 which is used for checking a wavelength of light from the light source unit 31 discussed later is provided on the stage 2, being so tilted as to reflect the light emitted from the light source unit 31, having a predetermined incident angle, vertically upwards (i.e., towards the objective lens 457).

The control part 5 has an calculation part 51 for performing various computations, and various information acquired by the light shielding pattern imaging part 43, the spectroscope 42, the substrate imaging part 44 and the light receiving unit 32 is inputted to the calculation part 51. The light source 41, the light source unit 31 and the stage moving mechanism 21 are also connected to the control part 5, and the control part 5 controls these constituents to perform a measurement of a thickness of a film formed on the substrate 9 by the film thickness measurement apparatus 1.

In the film thickness measurement apparatus 1, when the film on the substrate 9 is relatively thin, the calculation part 51 performs a film thickness measurement by ellipsometry on the basis of the output indicating the polarization state from the ellipsometer 3, and when the film is relatively thick or multilayer one, the operation part 51 calculates a film thickness by obtaining spectral reflectance on the basis of the output indicating the spectral intensity from the light interference unit 4.

In the film thickness measurement apparatus 1, when the film thickness measurement is performed on the basis of the output on the polarization state from ellipsometer 3, check on the wavelength of the light emitted from the light source unit 31 (hereinafter, referred to as "laser wavelength calibration") is first performed and subsequently a foreign material inspection for inspecting the presence or absence of foreign material at a measurement position on the substrate 9 is performed. When it is confirmed that no foreign material exists (in other words, confirmed that it is possible to perform a film thickness measurement with precision at the measurement position on the substrate 9), the film thickness measurement is performed after measuring a tilt angle of the substrate 9. Discussion will be made below on an operation of the film thickness measurement apparatus 1 for measuring a thickness of a film on the substrate 9 by the ellipsometer 3 step by step.

Figure 2:
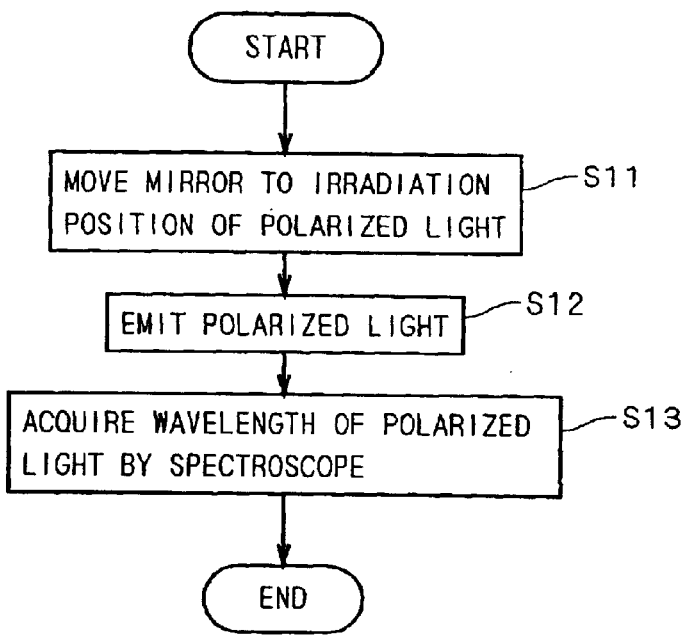
FIG. 2 is a flowchart showing a flow of laser wavelength calibration.

FIG. 2 is a flowchart showing a flow of laser wavelength calibration. In the laser wavelength calibration, first, the mirror 24 on the stage 2 is moved to an irradiation position of the polarized light by the stage moving mechanism 21 (Step S11), and emission of the polarized light from the light source unit 31 is started by control of the control part 5 (Step S12). With this, the light from the light source unit 31 is reflected by the mirror 24 and guided to the spectroscope 42 of the light interference unit 4.

In the spectroscope 42, the spectral intensity of the received light is acquired and as a result, the wavelength of the light beam emitted from the semiconductor laser 312 is substantially acquired. Data indicating the wavelength is outputted to the calculation part 51 and stored in a memory of the calculation part 51 (Step S13). The acquired wavelength of the light beam is used for the film thickness measurement by the ellipsometer 3.

Thus, in the film thickness measurement apparatus 1, it is possible to make switching between the substrate 9 and the mirror 24 to be positioned at the irradiation position of the light from the light source unit 31 by moving the stage 2 and during non-measurement periods, the light from the light source unit 31 is guided to the spectroscope 42 to acquire the wavelength of the light beam (i.e., the polarized light). This allows the film thickness measurement apparatus 1 to obtain the film thickness with high precision even if the wavelength of the light from the light source unit 31 is changed due to changes in ambient temperature or characteristics and the like of the constituents of the light source unit 31.

Instead of the mirror 24, a scatterer for scattering light may be used. The mirror 24 or the scatterer may be moved from a portion out of the stage 2 to the irradiation position of the polarized light.

Next discussion will be made on an inspection of foreign material on the substrate 9 in the film thickness measurement apparatus 1. In the foreign material inspection, an illumination light is emitted from the light source 41 and an image of the substrate 9 is acquired by the substrate imaging part 44 in advance, and the stage moving mechanism 21 moves the stage 2 on the basis of the image to align the measurement position of the substrate 9 to the irradiation position of the polarized light for ellipsometry.

Figure 3:
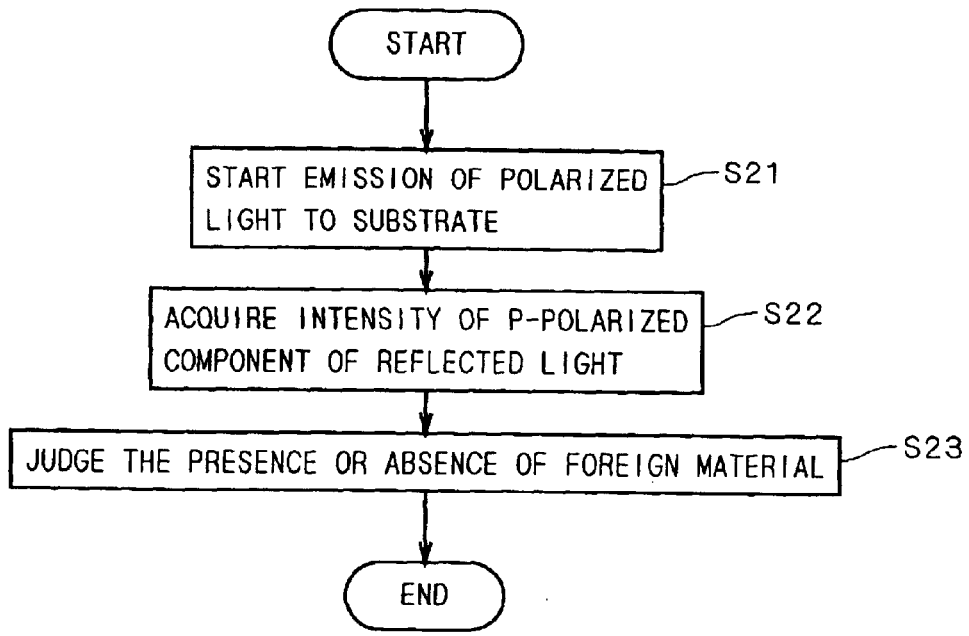
FIG. 3 is a flowchart showing a flow of foreign material inspection.

FIG. 3 is a flowchart showing a flow of foreign material inspection. First, emission of the polarized light is started from the light source unit 31 and the measurement position of the substrate 9 is irradiated with the polarized light entering at a predetermined incident angle (Step S21). At this time, an irradiation region of the substrate 9 which is irradiated with the polarized light is e.g., a circular one whose diameter is 10 μm. A reflected light of the polarized light from the substrate 9 is guided to the light receiving unit 32. At this time, the orientation of the rotating analyzer 321 of the light receiving unit 32 is fixed to transmit only a p-polarized component and the photodiode 322 acquires the intensity of only the p-polarized component of the reflected light (Step S22).

The calculation part 51 judges the presence or absence of foreign material on the substrate 9 on the basis of the intensity of the light entering from the light receiving unit 32 (Step S23). For example, when the incident angle of the polarized light to the substrate 9 is 72 to 80 degrees, if no foreign material exists at the irradiation position of the light on the substrate 9, almost no p-polarized component exists in the reflected light from the substrate 9. On the other hand, if some foreign material exists, the p-polarized component becomes relatively large. Then, the calculation part 51 judges that some foreign material exists when the p-polarized component is detected.

Thus, in the film thickness measurement apparatus 1, the intensity of the p-polarized component of the light which is emitted from the light source unit 31 and reflected by the substrate 9 is acquired and the calculation part 51 judges the presence or absence of foreign material on the substrate 9 on the basis of the intensity of the p-polarized component. As a result, the film thickness measurement apparatus 1 can easily inspect the presence or absence of foreign material.

Though it is possible to judge the presence or absence of foreign material on the substrate 9 by comparing a cycle intensity signal which is part of information indicating the polarization state acquired in film thickness measurement as discussed later with a cycle signal which is calculated in advance, in this case, it is necessary to make one rotation of the rotating analyzer 321 in order to acquire the polarization state and this deteriorates throughput. On the other hand, in the film thickness measurement apparatus 1, since the orientation of the rotating analyzer 321 is fixed during inspection, it is possible to quickly perform the foreign material inspection.

Even when the incident angle of the light from the light source unit 31 is out of the range from 72 to 80 degrees or when the light from the light source unit 31 is not polarized, it is possible to judge the presence or absence of foreign material from the change in intensity of the p-polarized component which is acquired by the light receiving unit 32. In the film thickness measurement apparatus 1, however, it is possible to inspect the presence or absence of foreign material with high sensitivity by making the polarized light enter at the incident angle of 72 to 80 degrees.

When it is confirmed that no foreign material exists at the measurement position on the substrate 9, the tilt angle of the substrate 9 to a horizontal surface (i.e., XY plane of FIG. 1) is subsequently measured. First, emission of the illumination light is started from the light source 41, the light shielding pattern imaging part 43 performs an imaging and image data of the light shielding pattern 453a is outputted to the calculation part 51.

As discussed earlier, the position of the light shielding pattern imaging part 43 is optically conjugate to the light shielding pattern 453a through the surface of the substrate 9 (the light shielding pattern imaging part 43 is positioned almost at an objective pupil position since the light shielding pattern 453a is positioned almost at an aperture stop position), and the position of the light shielding pattern in the image which is picked up by the light shielding pattern imaging part 43 is a position corresponding to the tilt angle of the substrate 9 (exactly, the tilt angle in the irradiation position of the illumination light).

The calculation part 51 stores the barycentric position (hereinafter, referred to as "reference position") of the light shielding pattern in the image at the time when the tilt angle is 0 degree in advance, and the tilt angle of the substrate 9 (exactly, a vector indicating the direction of the normal of the substrate 9) is obtained by calculating a distance (vector) between the barycentric position of the light shielding pattern in the acquired image and the reference position.

Specifically, assuming that a distance between the objective lens 457 and the surface of the substrate 9 (i.e., a distance which is kept constant by the AF detection unit 46) is f and a tilt angle of the substrate 9 is θ and the reflected light from the substrate 9 is received at the position of the objective lens 457 to acquire the image of the light shielding pattern 453a, the position of the light shielding pattern in the acquired image is moved by (f×tan(2θ)) in a direction corresponding to tilt from a condition where the tilt angle of the substrate 9 is 0 degree. Therefore, the image acquired by the light shielding pattern imaging part 43 is moved by a distance obtained by multiplying (f×tan(2θ)) by magnification toward the position of the objective lens 457 in the direction corresponding to the tilt and this distance is a distance between the above-discussed reference position and the detected barycentric position. Since the distance f is kept constant by the AF detection unit 46, the calculation part 51 can obtain the tilt angle θ of the substrate 9 with precision.

When the measurement of tilt angle is finished, the polarized light is emitted from the light source unit 31 to the substrate 9 and the polarization state of the reflected light is acquired by the light receiving unit 32. The calculation part 51 obtains a thickness of a film on the substrate 9 on the basis of the polarization state acquired by using the wavelength of the polarized light from the light source unit 31, which is acquired by laser wavelength calibration, and the precise incident angle which is obtained from the tilt angle (and tilt direction). The polarization state of the reflected light from the substrate 9 may be acquired during measurement of the tilt angle.

Figure 4:
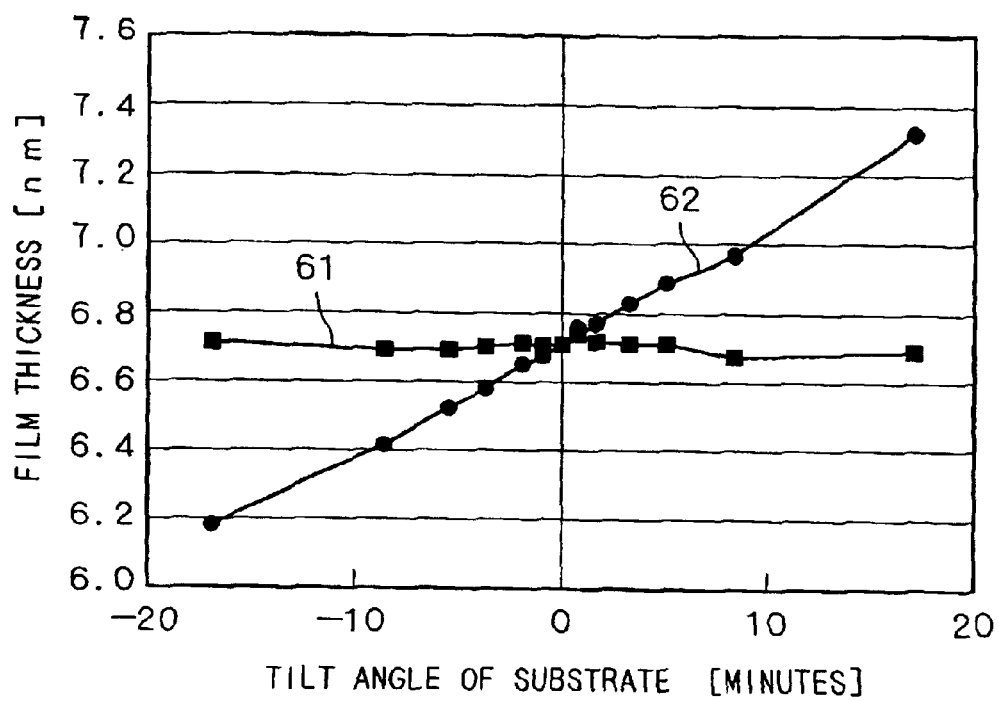
FIG. 4 is a graph showing a relation between a film thickness measurement result and a tilt angle.

FIG. 4 is a graph showing a film thickness calculated on the basis of the polarization state acquired while the tilt angle of one substrate 9 is changed. In FIG. 4, the line 61 indicates a result of calculation of film thickness by using the measured tilt angle and the line 62 indicates a result of calculation of film thickness without measurement of the tilt angle (i.e., assuming that the tilt angle is 0 second). It can be seen from FIG. 4 that when the measurement of tilt angle is not performed, the calculated film thickness varies due to the effect of tilt angle of the substrate 9, but when the measurement of tilt angle is performed, a constant film thickness can be calculated with high precision.

Thus, in the film thickness measurement apparatus 1, the image of the light shielding pattern 453a provided in the aperture stop part 453 is acquired by the light shielding pattern imaging part 43 to obtain the tilt angle of the substrate 9. Then, a thickness of a film on the substrate 9 is obtained with high precision by using the obtained tilt angle. This allows the film thickness measurement apparatus 1 to obtain a film thickness while appropriately correcting it without controlling the tilt of the substrate 9 even if the substrate 9 is tilted.

When the film thickness measurement is performed by the ellipsometer 3, it is not always necessary to perform all of the laser wavelength calibration, the foreign material inspection and the measurement of tilt angle. The laser wavelength calibration is not needed for every film thickness measurement and may be performed periodically (e.g., every predetermined number of measurements).

Next discussion will be made on another example of measurement of tilt angle of the substrate 9. In the measurement of tilt angle according to another example, the field stop part 454 is provided with a filter 454a to cut off a specific wavelength at a portion out of a predetermined region. For example, when the light source 41 uses a tungsten halogen lamp, the field stop part 454 is provided with the light shielding filter 454a for cutting off infrared light whose wavelength is 800 nm or more at a portion out of a center portion. A transmitting filter for transmitting only infrared light is attached to the light shielding pattern imaging part 43. This allows the infrared light whose wavelength is 800 nm or more to be emitted only to a microscopic region in the irradiation position of the illumination light of the substrate 9, corresponding to the center portion of the light shielding filter. The position of the microscopic region overlaps the irradiation position of the polarized light from the light source unit 31.

A reflected light of the illumination light is guided to the light shielding pattern imaging part 43 and only the reflected light corresponding to the microscopic region is received by the light shielding pattern imaging part 43 and an image of the light shielding pattern 453a is formed by the light from the microscopic region. The barycentric position of the image of the light shielding pattern 453a in the acquired image is moved from the reference position in accordance with a tilt angle of the microscopic region on the substrate 9 as discussed above. Therefore, the tilt angle of only the microscopic region can be obtained on the basis of a vector between the reference position and the detected barycentric position.

Since the whole irradiation region on the substrate 9 is irradiated with a light whose wavelength is 800 nm or less, the irradiation position of the illumination light on the substrate 9 can be confirmed with an image picked up by the substrate imaging part 44 and the irradiation position of the polarized light can be moved to a desired position on the substrate 9. Also in the film thickness measurement by the light interference unit 4 as discussed later, it is possible to perform a film thickness measurement using a light whose wavelength is 800 nm or less. It is natural that the light shielding filter 454a may be pulled out from an optical path in consideration of the film thickness measurement by the light interference unit 4.

When the measurement of tilt angle with respect to the microscopic region is finished, the polarized light from the light source unit 31 is emitted to the microscopic region on the substrate 9 and a reflected light of the polarized light is received by the light receiving unit 32 to acquire the polarization state of the reflected light. The calculation part 51 obtains a thickness of a film with respect to the microscopic region on the substrate 9 on the basis of the acquired polarization state by using the tilt angle with respect to the microscopic region.

Thus, in the film thickness measurement apparatus 1, it is possible to obtain a film thickness of the microscopic region on the substrate 9 more precisely by providing the light shielding filter 454a in the field stop part 454. The light shielding filter 454a is not necessarily positioned at the position of the field stop part 454 and may be disposed at a position almost optically conjugate to the field stop position in the optical path from the light source 41 to the substrate 9. This light shielding filter 454a has to cut off at least light of specific wavelength at a portion out of the portion corresponding to the microscopic region on the substrate 9, and may cut off light of all wavelengths.

Figure 5:
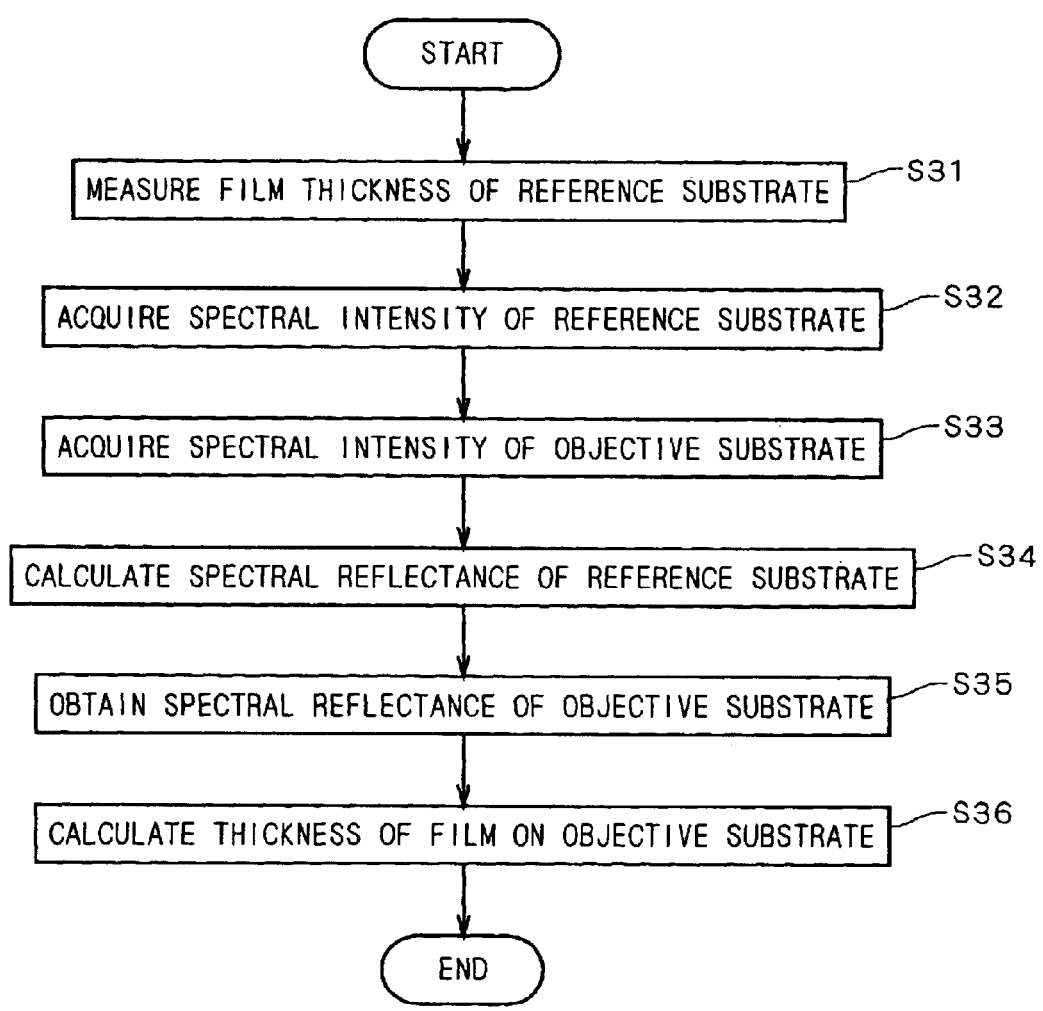
FIG. 5 is a flowchart showing a flow of operation for film thickness measurement on the basis of outputs from a light interference unit.

Next discussion will be made on an operation of the film thickness measurement apparatus 1 for film thickness measurement by obtaining spectral reflectance on the basis of an output indicating spectral intensity from the light interference unit 4 (specifically, measurement of thickness for a relatively thick film or a multilayer film). FIG. 5 is a flowchart showing a flow of operation of the film thickness measurement apparatus 1 for film thickness measurement using the light interference unit 4. Discussion will be made below along FIG. 5.

In the film thickness measurement by the light interferometric method, a reference object (hereinafter, referred to as "reference substrate") is used. As a reference substrate, a silicon substrate is usually used but on the reference substrate which is left in the atmosphere for a long time, a natural oxide film of silicon dioxide ($SiO_2$) is formed. Then, in the film thickness measurement apparatus 1, first, a thickness of the natural oxide film on the reference substrate is measured by ellipsometry using the ellipsometer 3 (Step S31).

Since a measurement by the ellipsometer 3 needs no reference object, as long as the wavelength, the incident angle (tilt angle at the irradiation position) and the like of an incident light is specified, it is possible to acquire the absolute value of film thickness (hereinafter, referred to as "absolute film thickness"). The acquired absolute film thickness of the reference substrate is stored in the calculation part 51.

When the measurement of absolute film thickness of the reference substrate is finished, in the light interference unit 4, the illumination light is emitted from the light source 41 and guided to the reference substrate by the optical system 45 and a reflected light from the reference substrate is guided to the spectroscope 42. Then, spectral intensity of the reflected light is acquired by the spectroscope 42 (Step S32) and spectral intensity data of the reference substrate is outputted to the calculation part 51. Subsequently, the substrate 9 which is a measurement object (hereinafter, referred to as "objective substrate 9" for distinction from the reference substrate) is disposed on the stage 2, the illumination light from the light source 41 is emitted to the measurement position on the objective substrate 9 and spectral intensity of the reflected light is acquired by the spectroscope 42 (Step S33). Spectral intensity data of the objective substrate 9 is outputted to the control part 5.

In the calculation part 51, (vertical) spectral reflectance of the reference substrate is calculated by theoretical computation from the absolute film thickness of the reference substrate which is acquired in Step S31 (Step S34). Hereinafter, the spectral reflectance obtained in the Step S34 is referred to as "theoretical spectral reflectance".

Subsequently, spectral reflectance of the objective substrate 9 is obtained from the spectral intensities of the reference substrate and the objective substrate 9 on the basis of the theoretical spectral reflectance of the reference substrate (Step S35). Herein, assuming that the theoretical spectral reflectance of the reference substrate is $Rc(\lambda)$, the spectral intensity of the reference substrate $Ic(\lambda)$, the spectral intensity of the objective substrate 9 is $Im(\lambda)$ and the spectral reflectance of the objective substrate 9 is $Rm(\lambda)$, the spectral reflectance $Rm(\lambda)$ of the objective substrate 9 is obtained by $(Rm(\lambda)=(Im(\lambda)/Ic(\lambda))\times Rc(\lambda))$. In other words, the spectral reflectance of the objective substrate 9 is obtained by multiplying the spectral intensity of the objective substrate 9 which is obtained by the light interference unit 4 by the ratio between the theoretical spectral reflectance of the reference substrate and the spectral intensity of the reference substrate. The calculation part 51 further calculates a thickness of a film on the objective substrate 9 from the spectral reflectance of the objective substrate 9 (Step S36).

Thus, in the film thickness measurement apparatus 1, the spectral reflectance of the reference substrate is calculated on the basis of the thickness of the film on the reference substrate which is measured by ellipsometry and the spectral reflectance of the objective substrate 9 is obtained with reference to the calculated spectral reflectance of the reference substrate. As a result, the film thickness measurement apparatus 1 can appropriately obtain the spectral reflectance of the objective substrate 9 without being affected by the natural oxide film on the reference substrate, to thereby calculate the film thickness with high precision.

The reference substrate is not necessarily a silicon substrate but may be a metal substrate or the like. The flow of the film thickness measurement shown in FIG. 5 may be changed as appropriate within the limits of the possible, and there may be a case, for example, where the spectral intensity of the reference substrate is acquired after calculation of the theoretical spectral reflectance of the reference substrate.

Though the preferred embodiment of the present invention has been discussed above, the present invention is not limited to the above-discussed preferred embodiment, but allows various variations.

While the foreign material inspection is performed in the film thickness measurement using the ellipsometer 3 in the above preferred embodiment, the constituents relating to the foreign material inspection may be used only for the foreign material inspection in a semiconductor manufacturing process and the like.

In the foreign material inspection, when a large foreign material or a number of foreign materials exist on the substrate 9, it is possible to also perform an inspection of foreign material by the spectroscope 42 since the spectroscope 42 of the light interference unit 4 receives the reflected light from the substrate 9.

The light shielding pattern 453a is not necessarily disposed at the position of the aperture stop part 453 but has only to be disposed at a position almost optically conjugate to the aperture stop position in the optical path from the light source 41 to the substrate 9. The light shielding pattern 453a may be a pattern for cutting off only light of specific wavelength, and in this case, a filter for transmitting only the light of specific wavelength may be provided in the light shielding pattern imaging part 43.

The polarized light emitted from the light source unit 31 to the substrate 9 is not limited to a circularly polarized light but various polarized lights (e.g., a linearly polarized light at 45 degrees) as appropriate may be used as necessary.

The substrate 9 is not limited to a semiconductor substrate but may be a glass substrate used for liquid crystal displays or other flat panel displays or the like.

While the invention has been shown and described in detail, the foregoing description is in all aspects illustrative and not restrictive. It is therefore understood that numerous modifications and variations can be devised without departing from the scope of the invention.

What is claimed is:

1. A film thickness measurement apparatus fox measuring a thickness of a film formed on an object, comprising:

a first light source for emitting a polarized light to an object;

a light receiving part for receiving a reflected light of said polarized light from said abject to acquire a polarization state of said reflected light;

an calculation part for obtaining a thickness of a film on said object on the basis of said polarization state;

a second light source for emitting an illumination light;

an optical system for guiding said illumination light to said object and guiding a reflected light of said illumination light from said object to a predetermined position;

a light shielding pattern disposed at a position almost optically conjugate to an aperture stop position on an optical path from said second light source to said object; and an imaging part for acquiring an image of said light shielding pattern formed on said predetermined position, wherein said calculation part obtains a tilt angle of said object on the basis of an output from said imaging part and obtains a thickness of said film from said polarization state, by using said tilt angle.

2. The film thickness measurement apparatus according to claim 1, further comprising:

a filter disposed at a position almost optically conjugate to a field stop position on an optical path from said second light source to said object, wherein said filter cuts off a light of at least specific wavelength at a portion out of a portion corresponding to a microscopic region on said object.

3. The film thickness measurement apparatus according to claim 1, wherein said calculation part obtains said tilt angle on the basis of a vector between a predetermined reference position and a barycentric position of an image of said light shielding pattern in an image indicated by said output from said imaging part.

* * * * *